US00PP31025P2

(12) United States Plant Patent
Van Swieten

(10) Patent No.: US PP31,025 P2
(45) Date of Patent: Nov. 5, 2019

(54) ***PHALAENOPSIS* ORCHID PLANT NAMED 'PHALFUZOP'**

(50) Latin Name: ***Phalaenopsis* hybrid**
Varietal Denomination: PHALFUZOP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,998

(22) Filed: Jun. 7, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFUZOP', particularly characterized by having yellow striped and netted flowers with yellow and red-purple lips, 1 to 3 peduncles that are long and sturdy, leaves that are obovate, and is propagated by meristem tissue culture, is disclosed.

3 Drawing Sheets

Genus and species: *Phalaenopsis* hybrid.
Variety denomination: 'PHALFUZOP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFUZOP'.

The new *Phalaenopsis* plant is a product of a planned breeding program conducted by the inventor in Bleiswijk, The Netherlands. The objective of this breeding program was to create a new *Phalaenopsis* plant with numerous attractive and unique yellow striped and netted flowers with yellow and red-purple lips, suitable for potted plant production.

The new *Phalaenopsis* plant 'PHALFUZOP' is a result of cross-pollination made by the inventor in February 2008 in Bleiswijk, The Netherlands of the proprietary female, or seed parent, *Phalaenopsis* hybrid 'PHALBUKAP' (U.S. Plant Pat. No. 25,445) with the proprietary male, or pollen parent, *Phalaenopsis* hybrid '22286-05' (unpatented).

The new *Phalaenopsis* was selected by the inventor as a single plant within the progeny of the stated cross-pollination in a controlled greenhouse in Bleiswijk, The Netherlands in December 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2018. 'PHALFUZOP' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFUZOP' as a new and distinct variety of *Phalaenopsis* plant.

1) Yellow striped and netted flowers with yellow and red-purple lips;
2) 1 to 3 peduncles;
3) Peduncle is long and sturdy; and
4) Shape of the leaf is obovate.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in April 2018. Colors in the photographs may differ from the color values cited in the detailed botanical description, which accurately describe the actual colors of the new variety.

DESCRIPTION OF THE NEW VARIETY

Figure 1:
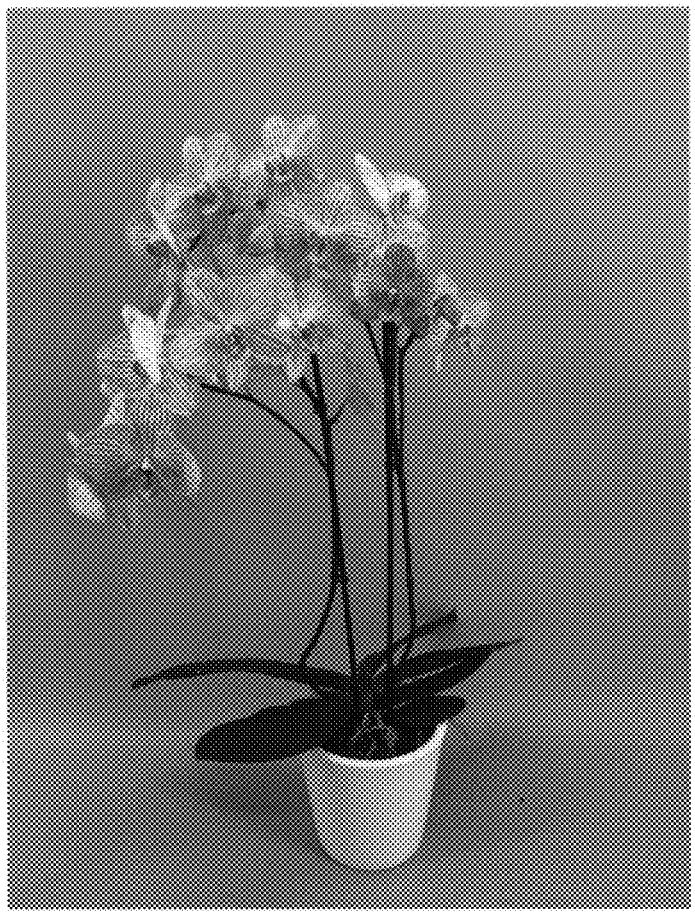
FIG. 1 shows the overall plant habit, including blooms, buds and foliage of 'PHALFUZOP'.
Figure 2:
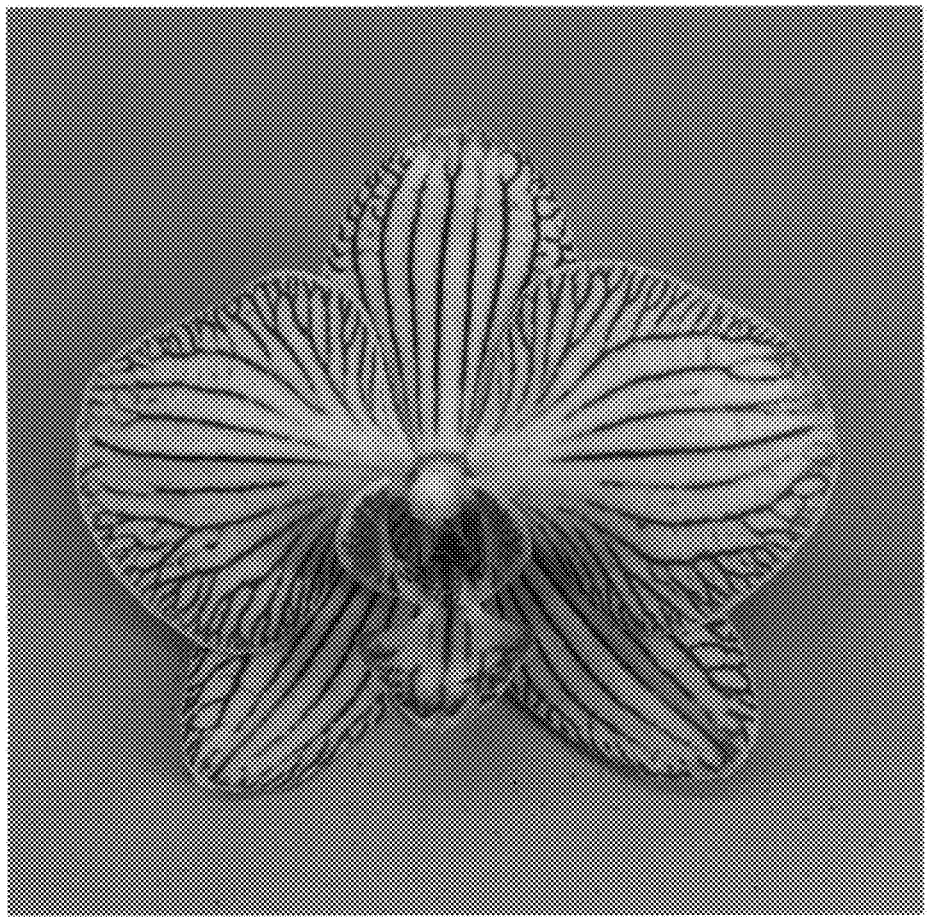
FIG. 2 shows a close-up of a flower of 'PHALFUZOP'.
Figure 3:
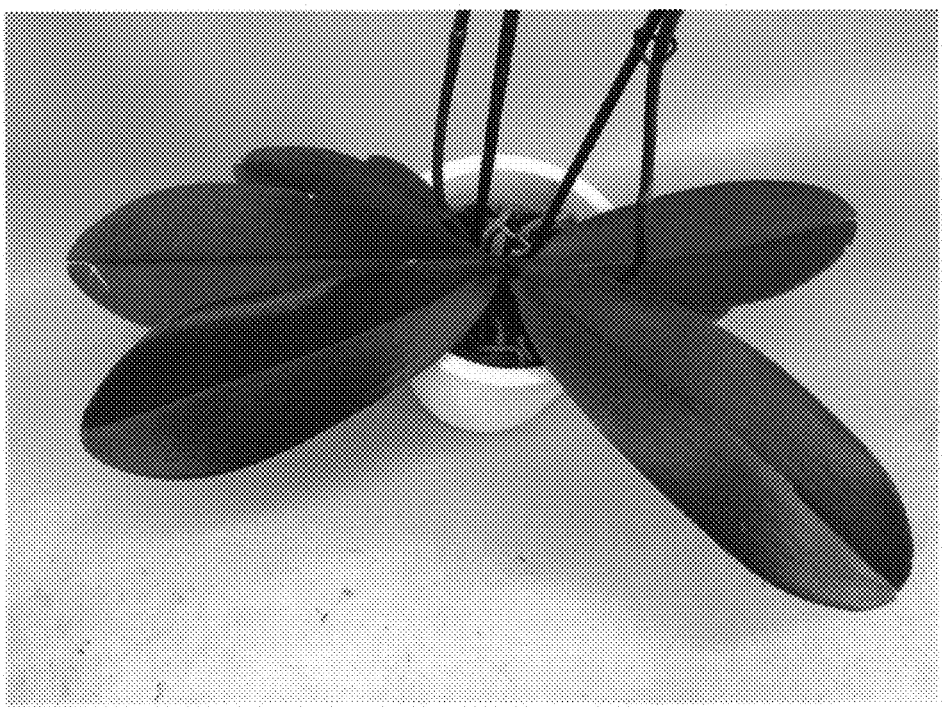
FIG. 3 shows an overhead view of the leaves of 'PHALFUZOP'.

The following detailed description sets forth the distinctive characteristics of 'PHALFUZOP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-

6000 lux natural light in a greenhouse in Bleiswijk, The Netherlands. Observations and measurements were made in April 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in a 12 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFUZOP'.

Parentage:

*Female parent*.—*Phalaenopsis* cultivar 'PHALBUKAP' (U.S. Plant Pat. No. 25,445).

*Male parent*.—*Phalaenopsis* cultivar '22286-05' (unpatented).

Propagation:

*Type*.—Meristem tissue culture.

Roots:

*Root description*.—Greyed-green colored roots (between RHS 190B and 190C) with branching lateral roots having green (RHS 146D) and red (RHS 182B) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Standard, green leaves, raceme to panicle.

*Height* (*from soil level to top of inflorescence*).—Approximately 58.0 cm to 63.0 cm.

*Width* (*measured from leaf tips*).—About 37.0 cm to 42.0 cm.

*Vigor*.—Moderate.

Leaves:

*Mature leaves*.—Quantity per plant: 8 to 10 leaves are produced before flowering. Length (fully expanded): 22.0 cm to 25.0 cm. Width: 8.0 cm to 8.5 cm. Shape: Obovate. Base shape: Moderately elongated. Apex: Obtuse unequal. Leaf blade angle with the petiole (measured from the horizontal position): Between 15 degrees and 30 degrees. Leaf margin: Entire. Color: Upper surface: RHS 147A. Lower surface: RHS 147B with diluting purple margin (RHS N77A). Texture (both upper and lower surfaces): Slightly rough. Thickness: 2.6 mm to 2.9 mm. Venation: Pattern: Parallel. Color of the midvein: Upper surface: RHS 147A. Lower surface: Diluting purple margin (RHS N77A).

Peduncle:

*Quantity per plant*.—1 to 3.

*Number of flowers per peduncle*.—11 to 14.

*Length*.—58.0 cm to 63.0 cm.

*Diameter*.—5.0 mm to 5.3 mm.

*Strength*.—Strong.

*Aspect*.—Upright to slightly pendant.

*Texture*.—Smooth.

*Color*.—Mix of green (RHS 146B) and brown (RHS 200A).

*Internode length*.—8.5 cm to 9.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 330.0 mm to 380.0 mm.

*Flowering time*.—First flowers can be expected 10 to 11 months after planting in a 12 cm (diameter) pot.

*Flower*.—Height: 78.0 mm to 83.0 mm. Diameter: 85.0 mm to 90.0 mm. Depth of lip: 24.0 mm to 26.0 mm.

*Flower longevity*.—On the plant: 15 to 22 weeks.

*Fragrance*.—Absent.

*Flower bud*.—Average size: Large. Length: 22.0 mm to 24.0 mm. Width: 15.0 mm to 17.0 mm. Shape: Egg shaped. Color: Green (mixture between RHS 146D and 144C) with diluting purple-red stripes (RHS 60B).

*Petals*.—Arrangement: Open/free. Shape: Semi-circular. Apex: Rounded asymmetric. Margin: Entire. Length (from base to tip): 40.0 mm to 42.0 mm. Width: 40.0 mm to 42.0 mm. Color (when fully opened): Upper surface: Basic color: Light greenish yellow (RHS 1C). Over color: Purple-red stripes and netting toward margin (RHS 60B). Lower surface: Basic color: Pale greenish yellow (RHS 1D). Over color: Diluting purple-red stripes and netting toward margin (RHS 60C).

*Dorsal sepal*.—Shape: Elliptic. Apex: Emarginated. Margin: Entire. Length (from base to tip): 45.0 mm to 47.0 mm. Width: 30.0 mm to 32.0 mm. Color (when fully opened): Upper surface: Basic color: Light greenish-yellow (RHS 1C). Over color: Purple-red stripes and netting toward margin (RHS 60B). Lower surface: Basic color: Pale greenish-yellow (RHS 1D). Over color: Touch of diluting yellowish green toward apex (RHS N144A) and diluting purple-red stripes and netting toward margin (RHS 60C).

*Lateral sepals*.—Shape: Ovate. Apex: Obtuse asymmetric. Margin: Entire. Length (from base to tip): 43.0 mm to 45.0 mm. Width: 27.0 mm to 29.0 mm. Color (when fully opened): Upper surface: Basic color: Light greenish yellow (RHS 1C). Over color: Purple-red stripes (RHS 60B). Lower surface: Basic color: Light yellow-green (RHS 145C). Over color: Diluting purple-red stripes (RHS 60C).

*Labellum* (*lip*).—Whiskers: Present. Length of whiskers: 12.0 mm to 14.0 mm. Color of whiskers: Red-purple (RHS N78A) with white margin (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 16.0 mm to 18.0 mm. Width: 9.0 mm to 11.0 mm. Color: Upper surface: Yellow (RHS 14A) at the base and margin on one side; dark red stripes and spots (RHS 59A) at the base; touch of white (RHS NN155C) in the middle and red-purple (RHS N78B) toward the other margin. Lower surface: White (RHS 155B) in the middle; pink (RHS N78D) to the front with a yellow edge (RHS 14A).

*Apical lobe*.—Shape: Rhombic. Margin: Entire. Length: 20.0 mm to 22.0 mm. Width: 19.0 mm to 21.0 mm. Color: Upper surface: Yellow (mixture between RHS 14B and 14C) at the base; white (RHS NN155C) and red-purple (mixture between RHS N78A and N78B) toward whiskers; dark red stripes (RHS 59A). Lower surface: White (RHS 155B) in the middle with pink (RHS N78D) toward the edge and an edge of deep orange-yellow (RHS 163A).

*Callus*.—Average size: Small. Height: 4.0 mm to 5.0 mm. Length: 4.0 mm to 5.0 mm. Width: 3.0 mm to 4.0 mm. Color: Yellow (RHS 14A) dotted (RHS 173A).

Reproductive organs:

*Column*.—Length: 8.0 mm to 10.0 mm. Diameter: 4.9 mm to 5.1 mm. Color: White (RHS NN155C) with a small light purple spot (RHS N78D) in the middle.

*Pollinia*.—Quantity: 2. Diameter: 0.9 mm to 1.0 mm. Color: Orange (RHS 24A).

*Ovary*.—Length: 10.0 mm to 12.0 mm. Diameter: 2.1 mm to 2.3 mm.

*Pedicel*.—Length: 33.0 mm to 35.0 mm. Diameter: 2.4 mm to 2.6 mm. Color: Green (RHS 146D); light green (between RHS 145C and 145D) and pinkish white (RHS N155C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFUZOP' differs from female parent plant 'PHALBUKAP' (U.S. Plant Pat. No. 25,445) in that 'PHALFUZOP' has green yellow flowers, purple whiskers with a white margin, and a white column with a small light purple spot in the middle, whereas 'PHALBUKAP' has white flowers, dark purple-red whiskers, and a purple-pink column. Additionally, 'PHALFUZOP' has narrower petals and shorter whiskers than 'PHALBUKAP'.

'PHALFUZOP' differs from male parent plant '22286-05' (unpatented) in that 'PHALFUZOP' has green yellow flowers that are striped, and purple whiskers with a white margin, whereas '22286-05' has yellow flowers that are spotted, and white whiskers. Additionally 'PHALFUZOP' has larger flowers, wider petals, and longer whiskers than '22286-05'.

'PHALFUZOP' is most similar to the commercial *Phalaenopsis* plants named 'PHALCILAK' (unpatented) and 'PHALVOBIS' (unpatented). 'PHALFUZOP' differs from the commercial variety 'PHALCILAK' in that 'PHALFUZOP' has a striped flower pattern and a white column with a small light purple spot in the middle, whereas 'PHALCILAK' has a netted and spotted flower pattern and a light reddish purple column with a small purple-pink region in the middle. Additionally, 'PHALFUZOP' has larger flowers and longer whiskers than 'PHALCILAK'.

'PHALFUZOP' differs from the commercial variety 'PHALVOBIS' in that 'PHALFUZOP' has a white column with a small light purple spot in the middle, whereas 'PHALVOBIS' has a purple-pink column. Additionally, 'PHALFUZOP' has larger flowers and longer whiskers than 'PHALVOBIS'.

I claim:

1. A new and distinct variety of *Phalaenopsis* plant named 'PHALFUZOP', substantially as described and illustrated herein.

* * * * *